United States Patent
Guo et al.

(10) Patent No.: US 10,316,303 B2
(45) Date of Patent: Jun. 11, 2019

(54) LACTONE HYDROLASE AND METHOD OF DEGRADING ALPHA-ZEARALENOL USING THE SAME

(71) Applicant: TIANJIN INSTITUTE OF INDUSTRIAL BIOTECHNOLOGY, CHINESE ACADEMY OF SCIENCES, Tianjin (CN)

(72) Inventors: Rey-Ting Guo, Tianjin (CN); Yingying Zheng, Tianjin (CN); Zhongxia Xu, Tianjin (CN); Chun-Chi Chen, Tianjin (CN); Wei Peng, Tianjin (CN); Weidong Liu, Tianjin (CN); Je-Ruei Liu, Tianjin (CN); Yanhe Ma, Tianjin (CN)

(73) Assignee: TIANJIN INSTITUTE OF INDUSTRIAL BIOTECHNOLOGY, CHINESE ACADEMY OF SCIENCES, Tianjin (CN)

( * ) Notice: Subject to any disclaimer, the term of this patent is extended or adjusted under 35 U.S.C. 154(b) by 19 days.

(21) Appl. No.: 15/366,370

(22) Filed: Dec. 1, 2016

(65) Prior Publication Data
US 2017/0191046 A1    Jul. 6, 2017

(30) Foreign Application Priority Data
Dec. 30, 2015    (CN) .......................... 2015 1 1015441

(51) Int. Cl.
| | |
|---|---|
| *C12N 9/18* | (2006.01) |
| *A23K 20/10* | (2016.01) |
| *A23K 10/30* | (2016.01) |
| *A23K 10/14* | (2016.01) |
| *A23L 5/20* | (2016.01) |

(52) U.S. Cl.
CPC ............... *C12N 9/18* (2013.01); *A23K 10/14* (2016.05); *A23K 10/30* (2016.05); *A23K 20/10* (2016.05); *A23L 5/25* (2016.08); *C12Y 301/01* (2013.01)

(58) Field of Classification Search
CPC ........................................................ C12N 9/18
See application file for complete search history.

(56) References Cited

PUBLICATIONS

PubChem alpha and beta zearalenols, structures. Downloaded Jul. 12, 2018.*
Peng et al, Crystal structure and substrate-binding mode of the mycoestrogen-detoxifying lactonase ZHD from Clonostachys rosea. Royal Society of Chemistry Adv., 2014, 4, 62321-25.*
Wei Peng et al., "Crystal structure and substrate-binding mode of the mycoestrogen-detoxifying lactonase ZHD from Clonostachys rosea," RSC Advances; 2014, 4, pp. 62321-62325.
Niaoko Takahashi-Ando et al., "A novel lactonohydrolase responsible for the detoxification of zearalenone: enzyme purification and gene cloning," Biochem. J.; 2002, 365, pp. 1-6.
NCBI GenBank: BAC02717; Jul. 4, 2002.

* cited by examiner

*Primary Examiner* — Sheridan Swope
(74) *Attorney, Agent, or Firm* — Kirton McConkie; Evan R. Witt

(57) ABSTRACT

A lactone hydrolase having improved activity towards α-zearalenol is disclosed. The lactone hydrolase has a modified amino acid sequence of SEQ ID NO: 5, wherein the modification is a substitution of valine at position 167 with histidine. A method of degrading α-zearalenol using such lactone hydrolase is also disclosed.

2 Claims, 7 Drawing Sheets
Specification includes a Sequence Listing.

ATGCGTACTCGTAGCACTATATCTACACCTAACGGTATCACATGGTACTATGAGCAAGAA
GGTACCGGTCCCGATGTGGTTTTGGTTCCCGATGGCCTAGGCGAATGTCAAATGTTCGAT
TCTTCTGTCTCTCAAATAGCCGCTCAAGGTTTCAGGGTCACTACCTTCGATATGCCAGGA
ATGTCCAGGTCCGCTAAGGCACCCCCGGAGACCTACACCGAAGTTACCGCACAAAAACTT
GCATCTTATGTAATATCTGTTTTGGATGCTTTAGACATTAAACATGCCACTGTCTGGGGT
TGTAGTAGTGGCGCTTCTACGGTTGTCGCTTTATTACTAGGTTATCCTGACAGAATTAGA
AACGCTATGTGCCATGAATTACCTACAAAGTTACTGGACCACTTATCAAATACAGCTGTA
CTGGAAGACGAAGAGATCTCTAAGATTTTGGCAAATGTGATGTTGAACGATGTATCAGGA
GGTAGTGAAGCATGGCAGGCCATGGGTGACGAGGTTCACGCAAGACTACATAAAAATTAC
CCAGTCTGGGCAAGAGGTTACCCTAGAACTATTCCGCCATCTGCTCCTGTAAAAGACTTG
GAAGCCTTAAGAGGAAAACCATTGGATTGGACAGTAGGCGCGGCTACACCTACAGAATCA
TTTTTTGATAATATTGTCACTGCGACTAAAGCCGGGGTGAATATTGGTTTATTGCCAGGG
ATGCATTTTCCATATGTGTCACATCCAGATGTTTTTGCCAAGTATGTTGTTGAGACTACT
CAGAAACACCTTTAA  - SEQ ID NO: 1

FIG. 3

MRTRSTISTPNGITWYYEQEGTGPDVVLVPDGLGECQMFD

SSVSQIAAQGFRVTTFDMPGMSRSAKAPPETYTEVTAQKL

ASYVISVLDALDIKHATVWGCSSGASTVVALLLGYPDRIR

NAMCHELPTKLLDHLSNTAVLEDEEISKILANVMLNDVSG

GSEAWQAMGDEVHARLHKNYPVWARGYPRTIPPSAPVKDL

EALRGKPLDWTVGAATPTESFFDNIVTATKAGVNIGLLPG

MHFPYVSHPDVFAKYVVETTQKHL    - SEQ ID NO: 2

FIG. 4

MAHHHHHHVDDDDKMRTRSTISTPNGITWYYEQEGTGPDV

VLVPDGLGECQMFDSSVSQIAAQGFRVTTFDMPGMSRSAK

APPETYTEVTAQKLASYVISVLDALDIKHATVWGCSSGAS

TVVALLGYPDRIRNAMCHELPTKLLDHLSNTAVLEDEEI

SKILAN<u>V</u>MLNDVSGGSEAWQAMGDEVHARLHKNYPVWARG

YPRTIPPSAPVKDLEALRGKPLDWTVGAATPTESFFDNIV

TATKAGVNIGLLPGMHFPYVSHPDVFAKYVVETTQKHL  - SEQ ID NO: 5

FIG. 5

| Mutation | V167H | |
|---|---|---|
| Forward Primer | 5'-TCTAAGATTTTGGCAAATcacATGTTGAACGATGTATCA-3' | (SEQ ID NO: 6) |
| Reverse Primer | 5'-TGATACATCGTTCAACATgtgATTTGCCAAAATCTTAGA-3' | (SEQ ID NO: 7) |

FIG. 6

MAHHHHHHVDDDDKMRTRSTISTPNGITWYYEQEGTGPDV
VLVPDGLGECQMFDSSVSQIAAQGFRVTTFDMPGMSRSAK
APPETYTEVTAQKLASYVISVLDALDIKHATVWGCSSGAS
TVVALLGYPDRIRNAMCHELPTKLLDHLSNTAVLEDEEI
SKILANHMLNDVSGGSEAWQAMGDEVHARLHKNYPVWARG
YPRTIPPSAPVKDLEALRGKPLDWTVGAATPTESFFDNIV
TATKAGVNIGLLPGMHFPYVSHPDVFAKYVVETTQKHL  - SEQ ID NO: 8

FIG. 7

LACTONE HYDROLASE AND METHOD OF DEGRADING ALPHA-ZEARALENOL USING THE SAME

FIELD OF THE INVENTION

The present invention relates to a lactone hydrolase, and more particularly to a lactone hydrolase having increased efficiency for degrading α-zearalenol.

BACKGROUND OF THE INVENTION

Mycotoxin is the secondary metabolites secreted by mold or other fungi. The growth of mold and the production of the mycotoxin may occur in various processes including the food's maturity, transportation, processing and storage. Feeds contaminated by mycotoxin can cause animal poisoning and affect their immune systems, and even cause serious public health problems. Mycotoxin pollution has been one of the key factors limiting the development of feed and breeding industry. A quarter of crops are contaminated by mycotoxin in varying degrees in the USA and Canada every year, giving rise to a loss of 50 hundred million dollars in feed and breeding industry. The direct losses caused by mycotoxin in China reaches 100 hundred million RMB every year. Even worse situation occurs in south China due to the humid climate.

In order to get rid of the damage to breeding industry, various physical and chemical methods have been developed to absorb or degrade the mycotoxin in feed. Currently, the most popular methods are to remove the mycotoxin by absorption. However, the absorbent is often not selective, resulting in the loss of other nutrients. In addition, mycotoxin excreted from the body can cause secondary pollution. In contrast, the biological detoxification, using enzymes to specifically degrade mycotoxin in mild conditions, with no involvement of hazard chemicals and no loss of nutrients, is considered to be the best method. Developing high efficiency mycotoxin degrading enzymes is the most important way to solve the problems of mycotoxin pollution and to recover the great loss in feed and breeding industry.

Zearalenone (ZEN) is a kind of estrogen-like toxin produced by *Fusarium* specie, possessing the resorcylic acid lactone structure (as shown in FIG. 1). ZEN is one of the three most seriously spread mycotoxin, identified firstly in moldy corn by Baldwin (Caldwell, R. W., Tuite, J., Stob, M., Baldwin, R., Zearalenone production by *Fusarium* species. *Applied Microbiology*, 1970, 20 (1), 31-4). ZEN is mainly existed in corn, wheat, barley, and millet, etc, and can cause the estrogen disordering such as precocity and reproductive cycle disordering, bringing huge losses to crop farming and breeding industry. In addition, ZEN also has a strong carcinogenicity and can cause breast cancer and esophageal cancer. There are six common natural derivatives of ZEN, of which zearalenol (ZOL, as shown in FIG. 1) is often coexisted with ZEN. ZOL has two isomers, α-ZOL and β-ZOL (FIG. 1 shows a generic representation of ZOL comprising α-ZOL and β-ZOL), of which α-ZOL is the major form with a 30-fold higher toxicity than ZEN.

Naoko Takahashi-Ando (Takahashi-Ando, N., Kimura, M., Kakeya, H., Osada, H., Yamaguchi, I., A novel lactonohydrolase responsible for the detoxification of zearalenone: enzyme purification and gene cloning. *The Biochemical Journal* 2002, 365 (Pt 1), 1-6) identified a lactone hydrolase ZHD101 from *Gliocladium roseum*, which becomes the most extensively studied ZEN degradation enzyme currently. ZHD101 hydrolyzes the lactone bond in the resorcylic acid lactone structure, opening the ring structure into a straight chain structure (as shown in FIG. 2), which further spontaneously decarboxylized and isomerized to form the final product. The hydrolysis product cannot combine with estrogen receptors, thereby eliminating toxicity. The gene of ZHD101 has been successfully expressed in heterologous hosts. However, it was found that the α-ZOL was still remained in the solution after ZEN had been completely hydrolyzed, due to the lower activity of ZHD101 towards α-ZOL. Since α-ZOL has an even stronger toxicity than ZEN, a huge amount of ZHD101 is needed to remove α-ZOL and to achieve the complete detoxification. Therefore, it is of great value to improve the degradation activity of ZHD101 towards high toxic α-ZOL.

Therefore, in order to improve the efficiency of detoxification of zearalenone and the derivatives, the present invention intends to increase the activity of ZHD101 towards α-ZOL by genetic modification, while maintaining the activity towards ZEN.

SUMMARY OF THE INVENTION

An object of the present invention is to modify a current lactone hydrolase ZHD101 by means of structural analysis and site-directed mutagenesis to efficiently improve its activity towards α-ZOL, which is a natural derivative of ZEN and has high toxicity, improve its detoxification efficiency, and further increase its economic value of industrial application.

An another object of the present invention is to provide a method of degrading α-ZOL by using the modified ZHD101 mutant to degrade α-ZOL so as to increase the degradation efficiency towards α-ZOL.

According to an aspect of the present invention, there is provided a lactone hydrolase comprising a modified amino acid sequence of SEQ ID NO: 5, wherein the modification is a substitution of valine at position 167 with histidine. The amino acid sequence of SEQ ID NO: 5 adds a pET46 vector sequence of 14 amino acids in N terminal of SEQ ID NO: 2, and the amino acid sequence of SEQ ID NO: 2 is encoded by zhd101 gene isolated from *Gliocladium roseum*. The lactone hydrolase has a full length amino acid sequence of SEQ ID NO: 8, and is used to increase the degradation efficiency towards α-zearalenol.

According to an another aspect of the present invention, there is provided a method of degrading α-zearalenol comprising a step of using a lactone hydrolase to degrade α-zearalenol, wherein the lactone hydrolase comprises a modified amino acid sequence of SEQ ID NO: 5, and the modification is a substitution of valine at position 167 with histidine. The amino acid sequence of SEQ ID NO: 5 adds a pET46 vector sequence of 14 amino acids in N terminal of SEQ ID NO: 2, and the amino acid sequence of SEQ ID NO: 2 is encoded by zhd101 gene isolated from *Gliocladium roseum*. The lactone hydrolase has a full length amino acid sequence of SEQ ID NO: 8.

The above objects and advantages of the present invention will become more readily apparent to those ordinarily skilled in the art after reviewing the following detailed description and accompanying drawings, in which:

BRIEF DESCRIPTION OF THE DRAWINGS

FIG. 3 shows the nucleotide sequence of ZHD101;

FIG. 4 shows the amino acid sequence of ZHD101;

FIG. 5 shows the amino acid sequence of ZHD101 expressed by pET46 vector;

FIG. 6 shows the sequences of the mutagenic primers;

FIG. 7 shows the amino acid sequence of the mutant ZHD101; and

DETAILED DESCRIPTION OF THE PREFERRED EMBODIMENT

Figure 1:
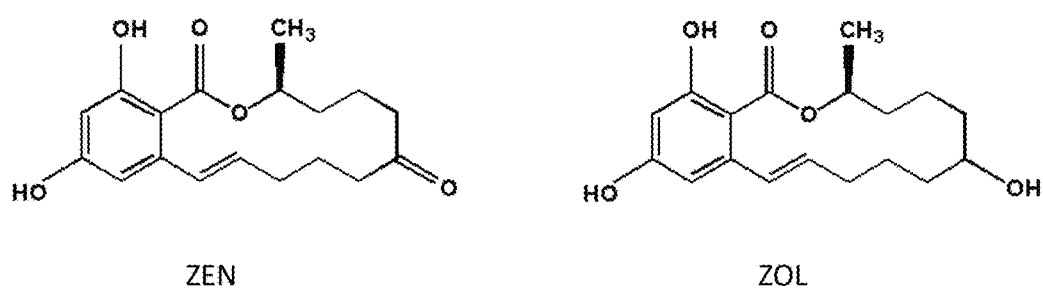
FIG. 1 shows the structures of ZEN and ZOL.
Figure 2:
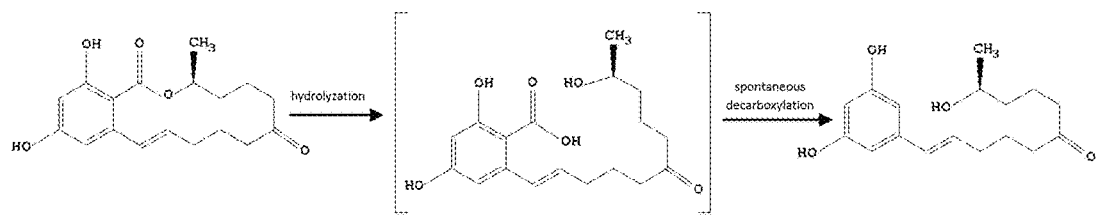
FIG. 2 shows the hydrolyzation reaction of ZHD101 towards ZEN.
Figure 8:
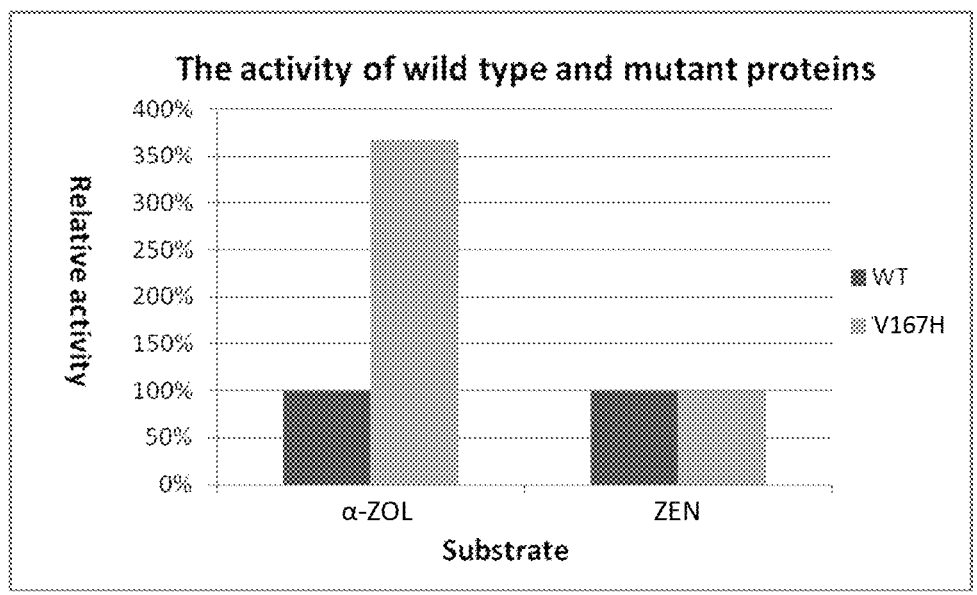
FIG. 8 shows the activity analysis of the wild type and the mutant lactone hydrolase ZHD101.

The present invention will now be described more specifically with reference to the following embodiments. It is to be noted that the following descriptions of preferred embodiments of this invention are presented herein for purpose of illustration and description only; it is not intended to be exhaustive or to be limited to the precise form disclosed.

In order to improve the industrial application of ZHD101, the present invention cloned the zhd101 gene from *Gliocladium roseum*, which encodes a lactone hydrolase. By studying the molecular structure, a novel residue interacting with substrates in the catalytic site is mutated to improve the activity towards α-ZOL. Following are the details of engineering the lactone hydrolase and description of the improved lactone hydrolase.

First, the zhd101 gene from *Gliocladium roseum* was selected as the target gene, which consists of 795 base pairs (SEQ ID NO: 1, as shown in FIG. 3) and encodes 264 amino acids (SEQ ID NO: 2, as shown in FIG. 4). The gene was amplified by polymerase chain reaction (PCR) with the forward primer 5'-GACGACGACAAGATGCGTACTCG-TAGCACTATATCTA-3' (SEQ ID NO: 3) and the reverse primer 5'-GAGGAGAAGCCCGGTTAAAGG TGTTTCT-GAGTAGTCTCA-3' (SEQ ID NO: 4). The PCR amplification product was inserted into pET46 vector by using the pET46EK/LIC kit. With this plasmid construction strategy, the expressed ZHD101 protein has a vector sequence of 14 amino acids in the N terminal of the protein, so the expressed ZHD101 protein includes 278 amino acids (SEQ ID NO: 5, as shown in FIG. 5).

In order to improve the activity of ZHD101 towards α-ZOL, the site-directed mutagenesis was used to modify ZHD101. pET46-zhd101 was used as the PCR template and the primers was shown in FIG. 6, in which the forward primer was numbered as SEQ ID NO: 6 and the reverse primer was numbered as SEQ ID NO: 7. In this mutation design, the 153rd residue in SEQ ID NO: 2 was mutated from valine to histidine. Since the protein expressed by pET46 vector has a vector sequence of 14 amino acids in the N terminal of the protein, the mutant protein has a modified amino acid sequence of SEQ ID NO: 5, wherein the modification is a substitution of valine at position 167 with histidine. The mutant protein is represented as V167H, and the amino acid sequence thereof was numbered as SEQ ID NO: 8, as shown in FIG. 7. Afterwards a restriction enzyme DpnI was added to remove the template plasmid at 37° C. The purified PCR product was transformed into *Escherichia coli* competent cells, and the clones was first screened by antibiotic and further checked by DNA sequencing.

The wild type and mutant clones were cultured in 5 ml LB culture as the primary culture seed, and then transferred to 200 ml secondary culture seed, and finally transferred into the 6 l culture, respectively. 1 mM IPTG was added to induce protein expression when OD of culture reached 0.6-0.8. After inducing for 3 hours, cells were harvested by centrifuge for 10 min at 6000 rpm. The cell pellets were resuspended in lysis buffer and disrupted by sonicator. The lysis solution was centrifuged for 30 min at 16000 rpm and the supernatant was collected for further purification. The Ni affinity chromatography and the DEAE anion exchange chromatography were used consecutively for purification with fast protein liquid chromatography (FPLC). Finally, the purified wild type and mutant proteins were obtained with the purity higher than 95%, and were stored at the concentration of 5 mg/ml at −80° C. in the solution of 25 mM Tris, 150 mM NaCl, pH 7.5.

The activities of the wild type and the mutant lactone hydrolase ZHD101, which are proteins of SEQ ID NO: 5 and SEQ ID NO: 8, respectively, towards ZEN and α-ZOL were determined to verify the difference therebetween. The assay of lactone hydrolase was shown as following.

The assay solution (210 μl) contains 5 μl substrate (5 mg/ml ZEN or 5 mg/ml α-ZOL) and 5 μl enzyme (0.25 mg/ml ZHD101, wild type or mutant) in the solution of 25 mM Tris, 150 mM NaCl, pH 7.5. After incubated for 10 min at 30° C., 50 μl 1 N HCl and 300 μl methanol were added to stop the reaction. 20 μl assay solution was tested by HPLC. The sample was eluted by 60% acetonitrile at the rate of 0.6 ml/min and the absorbance was detected at 254 nm. The amount of residual substrate was calculated according to the peak area. All data were determined three times and the average values were adopted.

FIG. 8 shows the activity analysis of the wild type and the mutant lactone hydrolase ZHD101. After Val167 was mutated to His, the activity towards α-ZOL of the mutant protein (V167H) was 3.7 times of that of the wild type (WT). Meantime, the activity towards ZEN was maintained in the mutant protein. These results showed that the mutant V167H improved the activity towards α-ZOL and maintained the activity towards ZEN.

From the above, in order to increase the detoxification efficiency, the key residue in the catalytic site of ZHD101 was mutated to increase the activity towards α-ZOL. According to the present invention, the mutant V167H can increase the activity towards α-ZOL, and the activity of the mutant V167H towards α-ZOL was increased by 3.7 times, while the activity of the mutant V167H towards ZEN remains the same when compared with the wild type. In other words, the present invention also provides a method of degrading α-ZOL by using the mutant V167H to degrade α-ZOL so as to increase the degradation efficiency towards α-ZOL. Therefore, the mutagenesis chosen by structural analysis of the present invention can obviously increase the detoxification efficiency of the lactone hydrolase ZHD101 and further enhance its application value in feed industry.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A method of degrading α-zearalenol comprising steps of:
   (a) cloning zhd101 gene into pET46 vector to form pET46-zhd101 clone which is capable of expressing the protein of SEQ ID NO: 5;
   (b) substituting valine at position 167 in SEQ ID NO: 5 with histidine by site-directed mutagenesis and expressing the protein of SEQ ID NO: 8; and
   (c) incubating α-zearalenol with the protein of SEQ ID NO: 8 to degrade α-zearalenol.

2. The method according to claim 1 wherein the zhd101 gene is isolated from *Gliocladium roseum*.

* * * * *

SEQUENCE LISTING

<160> NUMBER OF SEQ ID NOS: 8

<210> SEQ ID NO 1
<211> LENGTH: 795
<212> TYPE: DNA
<213> ORGANISM: Gliocladium roseum

<400> SEQUENCE: 1

```
atgcgtactc gtagcactat atctacacct aacggtatca catggtacta tgagcaagaa      60
ggtaccggtc ccgatgtggt tttggttccc gatggcctag gcgaatgtca aatgttcgat     120
tcttctgtct ctcaaatagc cgctcaaggt ttcagggtca ctaccttcga tatgccagga     180
atgtccaggt ccgctaaggc accccggag acctacaccg aagttaccgc acaaaaactt     240
gcatcttatg taatatctgt tttggatgct ttagacatta acatgccac tgtctgggt      300 tgtagtagtg gcgcttctac ggttgtcgct ttattactag gttatcctga cagaattaga     360
aacgctatgt gccatgaatt acctacaaag ttactggacc acttatcaaa tacagctgta     420
ctggaagacg aagagatctc taagattttg gcaaatgtga tgttgaacga tgtatcagga     480
ggtagtgaag catggcaggc catgggtgac gaggttcacg caagactaca taaaaattac     540
ccagtctggg caagaggtta ccctagaact attccgccat ctgctcctgt aaaagacttg     600
gaagccttaa gaggaaaacc attggattgg acagtaggcg cggctacacc tacagaatca     660
ttttttgata tattgtcac tgcgactaaa gccggggtga atattggttt attgccaggg     720
atgcattttc catatgtgtc acatccagat gttttttgcca agtatgttgt tgagactact     780
cagaaacacc tttaa                                                       795
```

<210> SEQ ID NO 2
<211> LENGTH: 264
<212> TYPE: PRT
<213> ORGANISM: Gliocladium roseum

<400> SEQUENCE: 2

```
Met Arg Thr Arg Ser Thr Ile Ser Thr Pro Asn Gly Ile Thr Trp
1               5                   10                  15

Tyr Tyr Glu Gln Glu Gly Thr Gly Pro Asp Val Val Leu Val Pro
                20                  25                  30

Asp Gly Leu Gly Glu Cys Gln Met Phe Asp Ser Ser Val Ser Gln
                35                  40                  45

Ile Ala Ala Gln Gly Phe Arg Val Thr Thr Phe Asp Met Pro Gly
                50                  55                  60

Met Ser Arg Ser Ala Lys Ala Pro Pro Glu Thr Tyr Thr Glu Val
                65                  70                  75

Thr Ala Gln Lys Leu Ala Ser Tyr Val Ile Ser Val Leu Asp Ala
                80                  85                  90

Leu Asp Ile Lys His Ala Thr Val Trp Gly Cys Ser Ser Gly Ala
                95                  100                 105

Ser Thr Val Val Ala Leu Leu Leu Gly Tyr Pro Asp Arg Ile Arg
                110                 115                 120

Asn Ala Met Cys His Glu Leu Pro Thr Lys Leu Leu Asp His Leu
                125                 130                 135

Ser Asn Thr Ala Val Leu Glu Asp Glu Ile Ser Lys Ile Leu
                140                 145                 150

Ala Asn Val Met Leu Asn Asp Val Ser Gly Gly Ser Glu Ala Trp
                155                 160                 165
```

-continued

Gln Ala Met Gly Asp Glu Val His Ala Arg Leu His Lys Asn Tyr
                170                 175                 180

Pro Val Trp Ala Arg Gly Tyr Pro Arg Thr Ile Pro Pro Ser Ala
            185                 190                 195

Pro Val Lys Asp Leu Glu Ala Leu Arg Gly Lys Pro Leu Asp Trp
        200                 205                 210

Thr Val Gly Ala Ala Thr Pro Thr Glu Ser Phe Phe Asp Asn Ile
    215                 220                 225

Val Thr Ala Thr Lys Ala Gly Val Asn Ile Gly Leu Leu Pro Gly
230                 235                 240

Met His Phe Pro Tyr Val Ser His Pro Asp Val Phe Ala Lys Tyr
            245                 250                 255

Val Val Glu Thr Thr Gln Lys His Leu
        260

<210> SEQ ID NO 3
<211> LENGTH: 37
<212> TYPE: DNA
<213> ORGANISM: Artificial Sequence
<220> FEATURE:
<223> OTHER INFORMATION: Synthetically generated primer

<400> SEQUENCE: 3
gacgacgaca agatgcgtac tcgtagcact atatcta                              37

<210> SEQ ID NO 4
<211> LENGTH: 39
<212> TYPE: DNA
<213> ORGANISM: Artificial Sequence
<220> FEATURE:
<223> OTHER INFORMATION: Synthetically generated primer

<400> SEQUENCE: 4
gaggagaagc ccggttaaag gtgtttctga gtagtctca                            39

<210> SEQ ID NO 5
<211> LENGTH: 278
<212> TYPE: PRT
<213> ORGANISM: Artificial Sequence
<220> FEATURE:
<223> OTHER INFORMATION: adding a vector sequence of 14 amino acids in N
      terminal of SEQ ID NO: 2

<400> SEQUENCE: 5

Met Ala His His His His His His Val Asp Asp Asp Asp Lys Met
1               5                   10                  15

Arg Thr Arg Ser Thr Ile Ser Thr Pro Asn Gly Ile Thr Trp Tyr
            20                  25                  30

Tyr Glu Gln Glu Gly Thr Gly Pro Asp Val Val Leu Val Pro Asp
        35                  40                  45

Gly Leu Gly Glu Cys Gln Met Phe Asp Ser Ser Val Ser Gln Ile
    50                  55                  60

Ala Ala Gln Gly Phe Arg Val Thr Thr Phe Asp Met Pro Gly Met
65                  70                  75

Ser Arg Ser Ala Lys Ala Pro Pro Glu Thr Tyr Thr Glu Val Thr
            80                  85                  90

Ala Gln Lys Leu Ala Ser Tyr Val Ile Ser Val Leu Asp Ala Leu
        95                  100                 105

Asp Ile Lys His Ala Thr Val Trp Gly Cys Ser Ser Gly Ala Ser
    110                 115                 120

Thr Val Val Ala Leu Leu Gly Tyr Pro Asp Arg Ile Arg Asn
                125                 130                 135

Ala Met Cys His Glu Leu Pro Thr Lys Leu Leu Asp His Leu Ser
                140                 145                 150

Asn Thr Ala Val Leu Glu Asp Glu Glu Ile Ser Lys Ile Leu Ala
                155                 160                 165

Asn Val Met Leu Asn Asp Val Ser Gly Ser Glu Ala Trp Gln
                170                 175                 180

Ala Met Gly Asp Glu Val His Ala Arg Leu His Lys Asn Tyr Pro
                185                 190                 195

Val Trp Ala Arg Gly Tyr Pro Arg Thr Ile Pro Pro Ser Ala Pro
                200                 205                 210

Val Lys Asp Leu Glu Ala Leu Arg Gly Lys Pro Leu Asp Trp Thr
                215                 220                 225

Val Gly Ala Ala Thr Pro Thr Glu Ser Phe Phe Asp Asn Ile Val
                230                 235                 240

Thr Ala Thr Lys Ala Gly Val Asn Ile Gly Leu Leu Pro Gly Met
                245                 250                 255

His Phe Pro Tyr Val Ser His Pro Asp Val Phe Ala Lys Tyr Val
                260                 265                 270

Val Glu Thr Thr Gln Lys His Leu
                275

<210> SEQ ID NO 6
<211> LENGTH: 39
<212> TYPE: DNA
<213> ORGANISM: Artificial Sequence
<220> FEATURE:
<223> OTHER INFORMATION: Synthetically generated primer

<400> SEQUENCE: 6
tctaagattt tggcaaatca catgttgaac gatgtatca                            39

<210> SEQ ID NO 7
<211> LENGTH: 39
<212> TYPE: DNA
<213> ORGANISM: Artificial Sequence
<220> FEATURE:
<223> OTHER INFORMATION: Synthetically generated primer

<400> SEQUENCE: 7
tgatacatcg ttcaacatgt gatttgccaa aatcttaga                            39

<210> SEQ ID NO 8
<211> LENGTH: 278
<212> TYPE: PRT
<213> ORGANISM: Artificial Sequence
<220> FEATURE:
<223> OTHER INFORMATION: a modified enzyme having a substitution of
      valine at position 167 with histidine from SEQ ID NO: 5

<400> SEQUENCE: 8

Met Ala His His His His His His Val Asp Asp Asp Asp Lys Met
1               5                   10                  15

Arg Thr Arg Ser Thr Ile Ser Thr Pro Asn Gly Ile Thr Trp Tyr
                20                  25                  30

Tyr Glu Gln Glu Gly Thr Gly Pro Asp Val Val Leu Val Pro Asp
                35                  40                  45

Gly Leu Gly Glu Cys Gln Met Phe Asp Ser Ser Val Ser Gln Ile

-continued

```
                  50                  55                  60
Ala Ala Gln Gly Phe Arg Val Thr Thr Phe Asp Met Pro Gly Met
                  65                  70                  75

Ser Arg Ser Ala Lys Ala Pro Pro Glu Thr Tyr Thr Glu Val Thr
                  80                  85                  90

Ala Gln Lys Leu Ala Ser Tyr Val Ile Ser Val Leu Asp Ala Leu
                  95                 100                 105

Asp Ile Lys His Ala Thr Val Trp Gly Cys Ser Ser Gly Ala Ser
                 110                 115                 120

Thr Val Val Ala Leu Leu Leu Gly Tyr Pro Asp Arg Ile Arg Asn
                 125                 130                 135

Ala Met Cys His Glu Leu Pro Thr Lys Leu Leu Asp His Leu Ser
                 140                 145                 150

Asn Thr Ala Val Leu Glu Asp Glu Ile Ser Lys Ile Leu Ala
                 155                 160                 165

Asn His Met Leu Asn Asp Val Ser Gly Gly Ser Glu Ala Trp Gln
                 170                 175                 180

Ala Met Gly Asp Glu Val His Ala Arg Leu His Lys Asn Tyr Pro
                 185                 190                 195

Val Trp Ala Arg Gly Tyr Pro Arg Thr Ile Pro Pro Ser Ala Pro
                 200                 205                 210

Val Lys Asp Leu Glu Ala Leu Arg Gly Lys Pro Leu Asp Trp Thr
                 215                 220                 225

Val Gly Ala Ala Thr Pro Thr Glu Ser Phe Phe Asp Asn Ile Val
                 230                 235                 240

Thr Ala Thr Lys Ala Gly Val Asn Ile Gly Leu Leu Pro Gly Met
                 245                 250                 255

His Phe Pro Tyr Val Ser His Pro Asp Val Phe Ala Lys Tyr Val
                 260                 265                 270

Val Glu Thr Thr Gln Lys His Leu
                 275
```